US011903988B2

(12) United States Patent
Rajendran

(10) Patent No.: US 11,903,988 B2
(45) Date of Patent: Feb. 20, 2024

(54) NATURAL PRODUCT COMPOSITIONS FOR MANAGEMENT OF CHOLESTEROL LEVELS

(71) Applicant: KARALLIEF INC, Cambridge, MA (US)

(72) Inventor: Krishna Rajendran, Cambridge, MA (US)

( * ) Notice: Subject to any disclaimer, the term of this patent is extended or adjusted under 35 U.S.C. 154(b) by 0 days.

(21) Appl. No.: 17/650,806

(22) Filed: Feb. 11, 2022

(65) Prior Publication Data

US 2023/0256044 A1 Aug. 17, 2023

(51) Int. Cl.
*A61K 36/328* (2006.01)
*A61K 36/82* (2006.01)
*A61P 3/06* (2006.01)
*A61K 36/9068* (2006.01)
*A61K 36/8962* (2006.01)
*A61K 36/9066* (2006.01)
*A61K 36/00* (2006.01)

(52) U.S. Cl.
CPC ............ *A61K 36/328* (2013.01); *A61K 36/82* (2013.01); *A61K 36/8962* (2013.01); *A61K 36/9066* (2013.01); *A61K 36/9068* (2013.01); *A61P 3/06* (2018.01)

(58) Field of Classification Search
None
See application file for complete search history.

(56) References Cited

U.S. PATENT DOCUMENTS

| 8,067,043 B2 * | 11/2011 | Managoli | A61P 9/00 |
| | | | 424/757 |
| 2019/0038576 A1 | 2/2019 | Baron et al. | |
| 2021/0283208 A1 | 9/2021 | Nirvanashetty et al. | |

FOREIGN PATENT DOCUMENTS

| CN | 001903350 A | * | 1/2007 |
| CN | 103751713 A | * | 4/2014 |
| KR | 20090054109 A | * | 5/2009 |
| KR | 2010064816 A | * | 6/2010 |
| KR | 2012103317 A | * | 9/2012 |
| KR | 101824217 B1 | * | 1/2018 |
| KR | 2001386 B1 | * | 7/2019 |
| KR | 2020145054 A | * | 12/2020 |
| KR | 2252130 B1 | * | 5/2021 |
| WO | WO2013122235 A1 | * | 8/2013 |

OTHER PUBLICATIONS (Anas et al. ("Antihyperlipidemic activity of Commiphora mukul: A review", The Pharma Innovation Journal 2019; 8(1); 496-498) (Year: 2019).*

Kumar et al. ("PHOG MAG.: Research Article Antihyperlipidemic activity of Camellia sinensis leaves in Triton WR-1339 induced albino rats" Phico Mag. Vol 4 Issue 13, Jan.-Mar. 2008, p. 1) (Year: 2008).*
Of Sharma et al.("Effect of Fenugreek Sees Powder (*Trigonella foenum-graecum* L.) on Experimental Induced Hyperlipidemia in Rabbits", Journal of Dietary Supplements, vol. 14, 2017—Issue, abstract p. 1) (Year: 2017).*
Adam J. Nelson, Neha J. Pagidipati, Christopher B. Granger, "The SAMSON trial: using a placebo to improve medication tolerability", ESC, European Heart Journal—Cardiovascular Pharmacotherapy (2021) 7, e13.
Ama Moor VJ, Ndongo Amougou S, Ombotto S, Ntone F, Wouamba De, Ngo Nonga B, "Dyslipidemia in Patients with a Cardiovascular Risk and Disease at the University Teaching Hospital of Yaounde, Cameroon", Int J Vasc Med 2017;2017:6061306.
*Arrow Intern., Inc.* v. *Spire Biomedical, Inc.*, 635 F.Supp.2d 46 (D. Mass. 2009), Civil Action No. 06-cv-11564-DPW, United States District Court, D, Massachusetts, Jul. 10, 2009.
Bogusław Okopień, Łukasz, Bułdak, Aleksandra Bołdys , "Benefits and risks of the treatment with fibrates—a comprehensive summary", Expert review of clinical pharmacology. Nov. 2, 2018;11(11):1099-112.
Cavero-Redondo I, et al., "Glycated haemoglobin A1c as a risk factor of cardiovascular outcomes and all-cause mortality in diabetic and non-diabetic populations: a systematic review and meta-analysis", BMJ Open 2017;7: e015945. doi:10.1139.
Centres for Disease Control and Prevention, "LDL and HDL Cholesterol: "Bad" and "Good" Cholestrol, 2020", Jan. 31, 2020.
Rafael A. Cox, Mario R., García-Palmieri, "Cholesterol, Triglycerides, and Associated Lipoproteins", Walker HK, Hall WD, Hurst JW, eds. Clinical Methods: The History, Physical, and Laboratory Examinations, 3rd ed. Boston, MA: Butterworths; 1990. Chapter 31.
Gordon D.O. Lowe, Mark B. Pepys, "C-reactive protein and cardiovascular disease: weighing the evidence", Current Atherosclerosis Reports 2006, 8:421-428.
Green Chem, "Analysis of Camitechin in Kara Heart Formula by HPLC Method" (Cited in the specification).

(Continued)

*Primary Examiner* — Aaron J Kosar
*Assistant Examiner* — Randall O Winston
(74) *Attorney, Agent, or Firm* — Stonebridge IP, PLLC

(57) ABSTRACT

A composition includes *Commiphora mukul* extract, *Camellia sinensis* extract, and *Trigonella foenum*-graecum extract. The composition may further include *Allium sativum* extract, *Zingiber officinale* extract, and *Cinnamomum verum* extract. The composition may include *Commiphora mukul* extract at about 24%-36% by weight of the total composition, the *Allium sativum* extract at about 20%-30% by weight of the total composition, the *Camellia sinensis* extract at about 12%-18% by weight of the total composition, the *Trigonella foenum*-graecum extract at about 12%-18% by weight of the total composition, the *Zingiber officinale* extract at about 8%-12% by weight of the total composition, and the *Cinnamomum verum* extract at about 4%-6% by weight of the total composition. The disclosure further provides methods of treating hyperlipidemia using the disclosed compositions.

17 Claims, No Drawings

(56) References Cited

OTHER PUBLICATIONS

Green Chem, "Analysis of Commiphytes in Kara Heart Formula by HPLC Method" (Cited in the specification).

Green Chem, "Analysis of Zinzirols in Kara Heart Formula by HPLC Method" (Cited in the specification).

Hasani-Ranjbar et al., "The Efficacy and Safety of Herbal Medicines Used in the Treatment of Hyperlipidemia; A Systematic Review", Current Pharmaceutical Design, 2010, 16, 2935-2947.

Lee Y, Siddiqui Wj, "Cholesterol levels", StarPearls Publishing 2019, Jul. 26, 2021.

Luc et al., "Value of HDL cholesterol, apolipoprotein A1, lipoprotein A1, and lipoprotein A-1/A-II in prediction of coronary heart disease", Arterioscler Thromb Vasc Biol 2002;22:1155-1161.

Mohammad Taha Jalali, Abdolhosain Mosavi Honomaror, Abdolkarim Rekabi, Mahmod Latifi, "Reference Ranges for Serum Total Cholesterol, HDL-Cholesterol, LDL-Cholesterol, and VLDL-Cholesterol and Triglycerides in Healthy Iranian Ahvaz Population", Ind J Clin Biochem (Jul.-Sep. 2013) 28(3):277-282.

Nancy L. Urizar, Amy B. Liverman, D'Nette T. Dodds, Frank Valentin Silva, Peter Ordentlich, Yingzhuo Yan, Frank J. Gonzalez, Richard A. Heyman, David J. Mangelsdorf, David D. Moore, "A natural product that lowers cholesterol as an antagonist ligand for FXR", Science May 31, 2002;296(5573):1703-6.

Robert H. Nelson, "Hyperlipidemia as a risk factor for cardiovascular disease", Prim Care Mar. 2013;40(1):195-211.

Rahim et al., "Serum Apo A-1 and its role as a biomarker of coronary artery disease", Cureus Dec. 2016; 8(12):e941, Published Dec. 24, 2016.

Singh et al., "Management of Hridroga (Cardiovascular Disease) with Simple Ayurvedic Drugs—A Review", Research & Reviews: A Journal of Ayurvedic Science, Yoga andNaturopathy 2016;3(1):12-6.

Singh, Niaz, Ghosh, "Hypolipidemic and antioxidant effects of Commiphora mukul as an adjunct to dietary therapy in patients with hypercholesterolemia", Cardiovasc Drugs Therapy, 1994;8:659-664.

University of Rochester Medical Centre, Health Encyclopedia, "Apolipoprotein A", accessed May 7, 2021.

Veronica Azemawah, Mohammad Reza Movahed, Patrick Centuori, Ryan Penaflor, Pascal L. Riel, Steven Situ, Mehrdad Shadmehr, Mehrnoosh Hashemzadeh, "State of the Art Comprehensive Review of Individual Statins, Their Differences, Pharmacology, and Clinical Implications", Cardiovascular drugs and therapy. Oct. 2019;33(5):625-39.

Who, "World Health Organization. Global Health Observatory data: Cholesterol, 2021", Jun. 21, 2021.

Wikipedia, the free encyclopedia, "Active ingredient", last edited Oct. 19, 2021.

Wikipedia, the free encyclopedia, "Camellia sinensis", last edited Nov. 30, 2021.

Wikipedia, the free encyclopedia, "Cholesterol", last edited Oct. 13, 2021.

Wikipedia, the free encyclopedia, "Cinnamomum verum", last edited Nov. 2, 2021.

Wikipedia, the free encyclopedia, "Commiphora wightii", last edited Nov. 19, 2021.

Wikipedia, the free encyclopedia, "Extraction (chemistry)", last edited Aug. 25, 2021.

Wikipedia, the free encyclopedia, "Fenugreek", last edited Dec. 2, 2021.

Wikipedia, the free encyclopedia, "Garlic", last edited Nov. 29, 2021.

Wikipedia, the free encyclopedia, Ginger, last edited Nov. 25, 2021.

Wikipedia, the free encyclopedia, "Hyperlipidemia", last edited Oct. 4, 2021.

Wikipedia, the free encyclopedia, "Mammal", last edited Oct. 18, 2021.

Wikipedia, the free encyclopedia, "Natural product", last edited Sep. 8, 2021.

Wikipedia, the free encyclopedia, "Route of administration", last edited Nov. 5, 2021.

Wikipedia, the free encyclopedia, "Therapy", last edited Nov. 21, 2021.

Hidekatsu Yanai, Hiroshi Yoshida, "Secondary dyslipidemia: its treatments and association with atherosclerosis", Glob Health Med Feb. 28, 2021;3(1):15-23.

Yu et al., "Effect of Guggulsterone and Cembranoids of Commiphora mukul on Pancreatic Phospholipase A2: Role in Hypocholesterolemia", J. Nat. Prod. 2009, 72, 24-28.

Wikipedia, the free encyclopedia, "Gingerol", last edited Oct. 4, 2021.

Wikipedia, the free encyclopedia, "Epigallocatechin gallate", last edited Aug. 16, 2021.

Wikipedia, the free encyclopedia, "Guggulsterone", last edited Jan. 27, 2021.

PCT Communication in Cases for Which No Other Form is Applicable (observation from third party) international appl. No. PCT/US2023/062416, issued Oct. 27, 2023.

Submitted With Third Party Observation dated Oct. 27, 2023 Int. App. No. US2023/062416, "Chai", Key Attributes of TKDL, AN2/324, Title of Traditional Knowledge Resource.

Submitted With Third Party Observation dated Oct. 27, 2023 Int. App. No. US2023062416, "Dhanyaka Guna", Key Attributes of TKDL, SL2/195, Title of Traditional Knowledge Resource.

Submitted With Third Party Observation dated Oct. 27, 2023 Int. App. No. US2023062416, "Guggulu Guna", Key Attributes of TKDL, MR1/227, Title of Traditional Knowledge Resource.

Submitted With Third Party Observation dated Oct. 27, 2023 Int. App. No. US2023062416, "Halwa -e- Narangi", Key Attributes of TKDL, MH3/25, Title of Traditional Knowledge Resource.

Submitted With Third Party Observation dated Oct. 27, 2023 Int. App. No. US2023062416, "Lasuna Guna", Key Attributes of TKDL, RS231153, Title of Traditional Knowledge Resource.

Submitted With Third Party Observation dated Oct. 27, 2023 Int. App. No. US2023062416, "Methi Guna", Key Attributes of TKDL, RS4/245, Title of Traditional Knowledge Resource.

Submitted With Third Party Observation dated Oct. 27, 2023 Int. App. No. US2023062416, "Sounth", Key Attributes of TKDL, JA7/129, Title of Traditional Knowledge Resource.

Submitted With Third Party Observation dated Oct. 27, 2023 Int. App. No. US2023062416, "Tvaca Guna", Key Attributes of TKDL, RS15/255, Title of Traditional Knowledge Resource.

Nabekura et al., "Effects of Natural Polyphenols on the Expression of Drug Efflux Transporter P-Glycoprotein in Human. Intestinal Cells", ACS Omega 2018, 3, 1621-1626.

PCT International Search Report, international appl. No. PCT/US2023/062416, dated Apr. 26, 2023.

PCT Written Opinion of the International Searching Authority, international appl. No. PCT/US2023/062416, dated Apr. 26, 2023.

Sharma et al., "Hypocholesterolemic and Antioxidant Potentials of Some Plants and Herbs: A Review", RRJZS / vol. 1 | Issue 2 | Oct.-Dec. 2013, e-ISSN: 2321-6190, p-ISSN: 2347-2294.

\* cited by examiner

NATURAL PRODUCT COMPOSITIONS FOR MANAGEMENT OF CHOLESTEROL LEVELS

BACKGROUND

Technical Field

This disclosure relates to compositions for hyperlipidemia, including cholesterol management in a mammal.

Description of Related Art

Most individuals with high cholesterol must currently take synthetic medications or pharmaceuticals that have significant short term and long-term side effects. Cholesterol management is a long-term chronic challenge, so patients often must take these medications over a long period of time for example, even many decades. Side effects, however, tend to get progressively worse over time.

Natural products, for example herbal extracts, offer potential long-term solutions since they tend to have fewer and less severe side effects. However, very few natural products for cholesterol management have been tested and proven for safety and efficacy. Many natural products are sold on the basis of traditional historical usage, but generally do not have rigorous modern-day science and testing to support their claims of efficacy.

Currently, there are medications available for managing cholesterol, however, the side-effects and costs associated with these medications are significant. The primary Adverse Events (AE) with statins, which were originally derived from fungi, are the statin-induced myopathies. AE for the fibrates, another class of drugs used to treat hyperlipidemia, include nausea, pain, cholelithiasis, cholecystitis, hepatic disorders, and clotting disorders. A natural product alternative to the available medications could provide a low-cost option with fewer and milder side-effects. Currently, there is no supplement proven to be safe and effective in treating hyperlipidemia.

Accordingly, there is a need for natural product compositions that provide proven safe and effective long-term solutions for cholesterol management that have fewer side effects compared to existing pharmaceuticals.

SUMMARY DISCLOSURE OF THE INVENTION

A composition for the treatment of hyperlipidemia in a mammal includes *Commiphora mukul* extract, *Camellia sinensis* extract, and *Trigonella foenum*-graecum extract. The composition may further include *Allium sativum* extract, *Zingiber officinale* extract, and *Cinnamomum verum* extract. The composition may include *Commiphora mukul* extract at about 24%-36% by weight of the total composition, the *Allium sativum* extract at about 20%-30% by weight of the total composition, the *Camellia sinensis* extract at about 12%-18% by weight of the total composition, the *Trigonella foenum*-graecum extract at about 12%-18% by weight of the total composition, the *Zingiber officinale* extract at about 8%-12% by weight of the total composition, and the *Cinnamomum verum* extract at about 4%-6% by weight of the total composition.

Methods of treating hyperlipidemia in a mammal are further disclosed which include administering a composition including *Commiphora mukul* extract, *Camellia sinensis* extract, and *Trigonella foenum*-graecum extract to a mammal in need thereof. The composition may further include *Allium sativum* extract, *Zingiber officinale* extract, and *Cinnamomum verum* extract.

Other features and aspects will be apparent from the following detailed description and the claims.

DETAILED DISCLOSURE OF THE INVENTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

Modes for Carrying Out the Invention

The present invention includes a unique herbal extract blend that supports cholesterol management. In embodiments, the invention is an herbal extract blend consisting of up to six herbal extracts standardized to specific active marker compounds. These extracts work synergistically together to provide strong results as demonstrated in a human clinical trial.

The extract may include a blend in powder form. In addition, the blend may include excipients; sometimes in small amounts. Extraction solvents to obtain the extracts may include water and alcohol. The extracts may be included in tablets/capsules/pills, food/beverages, and/or skin care products as nonlimiting examples.

A significant feature is the selection of a unique blend of herbal extracts that act synergistically with each other to provide strong results seen in human clinical trials as disclosed below. The blend may include a specific ratio of ingredients and the blend may include specific amounts of active compounds.

In embodiments, the disclosed compositions include *Commiphora mukul* extract, *Camellia sinensis* extract, and *Trigonella foenum*-graecum extract. In embodiments, the disclosed compositions may consist of or consist essentially of *Commiphora mukul* extract, *Camellia sinensis* extract, and *Trigonella foenum*-graecum extract. In embodiments, the disclosed compositions may include *Commiphora mukul* extract, *Camellia sinensis* extract, *Trigonella foenum*-graecum extract, *Allium sativum* extract, *Zingiber officinale* extract, and *Cinnamomum verum* extract. In embodiments, the disclosed compositions may consist of or consist essentially of *Commiphora mukul* extract, *Camellia sinensis* extract, *Trigonella foenum*-graecum extract, *Allium sativum* extract, *Zingiber officinale* extract, and *Cinnamomum verum* extract. In this case the composition can include the active ingredients stated above as well as other inactive ingredients, excipients, fillers, additives, vehicles, etc.

In embodiments, the disclosed compositions include *Commiphora mukul* extract at about 30% by weight, *Allium sativum* extract at about 25% by weight, *Camellia sinensis* extract at about 15% by weight, *Trigonella foenum*-graecum extract at about 15% by weight, *Zingiber officinale* extract at about 10% by weight, and *Cinnamomum verum* extract at about 5% by weight.

In embodiments, other herbal extracts can also be added to the composition and may provide an even more enhanced benefit. For example, Turmeric extract, Coriander extract, *Capsicum* annum extract, Horse chestnut extract, Rosehip extract, Radish extract, and/or *Citrus sinensis* extract. Other extracts known and commonly used in the herbal medicine art may also be added.

The amounts of extracts used in the disclosed compositions may vary in amounts ranging from about 1% to about 20% by weight and continue to provide compositions with a comparable level of efficacy.

Accordingly, a composition may include *Commiphora mukul* extract at about 24%-36% by weight of the total composition, the *Allium sativum* extract at about 20%-30% by weight of the total composition, the *Camellia sinensis* extract at about 12%-18% by weight of the total composition, the *Trigonella foenum*-graecum extract at about 12%-18% by weight of the total composition, the *Zingiber officinale* extract at about 8%-12% by weight of the total composition, and the *Cinnamomum verum* extract at about 4%-6% by weight of the total composition.

In embodiments, the product may be a blend of six herbal extracts. In one embodiment, each extract may be prepared individually and then the extracts combined in particular amounts to make a final product. For example, the *Commiphora mukul* extract may be prepared to include about 2.5% active substance Commiphytes by weight; the *Camellia sinensis* extract may be prepared to include about 40% by weight active substance Camitechins; the *Zingiber officinale* may include about 5% active substance Zinzirols by weight. The amounts of active substances(s) in the extracts may be determined by HPLC. As mentioned, the extracts may then be combined in a specific ratio to make a final product.

As one example, the level of active substance Camitechin in the combined blend of extracts may be about 6% by weight. In this case, the *Camellia sinensis* extract is prepared or processed to include about 40% active substance Camitechin. Thus, when combined in the final product with the other extracts, the *Camellia sinensis* extract may be about 15% by weight of the blend as described above. Accordingly, the amount of active substance Camitechin in the blend would be about 6%. The amounts of other active substances may be similarly calculated. The active substance Commiphytes may be about 0.75% of the product blend. The active substance Zinzirols may be about 0.5% of the product blend.

Glossary

*Commiphora mukul* extract derives from a flowering plant in the family Burseraceae. See e.g., *Commiphora wightii*, Wikipedia, the free encyclopedia, last edited 19 Nov. 2021, herein incorporated by reference. The extract can be obtained through extraction. See Example 1 and "Analysis of Commiphytes in Kara Heart Formula by HPLC method", Green Chem, herein incorporated by reference (IDS). See also, e.g., Extraction (chemistry), Wikipedia, the free encyclopedia, last edited 25 Aug. 2021, herein incorporated by reference; and e.g., Natural Product (isolation and purification), Wikipedia, the free encyclopedia, last edited 8 Dec. 2021, herein incorporated by reference.

*Camellia sinensis* extract a species of evergreen shrubs or small trees in the flowering plant family Theaceae. See e.g., *Camellia sinensis*, Wikipedia, the free encyclopedia, last edited 30 Nov. 2021, herein incorporated by reference. The extract can be obtained by extraction. See Example 1 and "Analysis of Camitechin in Kara Heart Formula by HPLC method", Green Chem, herein incorporated by reference (IDS). See also, e.g., Extraction (chemistry), Wikipedia, the free encyclopedia, last edited 25 Aug. 2021; and e.g., Natural Product (isolation and purification), Wikipedia, the free encyclopedia, last edited 8 Dec. 2021.

*Trigonella foenum*-graecum extract derives from a plant in the family Fabaceae. See e.g., Fenugreek, Wikipedia, the free encyclopedia, last edited to December 2021, herein incorporated by reference. The extract can be obtained by extraction. See Example 1. See e.g., Extraction (chemistry), Wikipedia, the free encyclopedia, last edited 25 Aug. 2021; and e.g., Natural Product (isolation and purification), Wikipedia, the free encyclopedia, last edited 8 Dec. 2021.

*Allium sativum* extract derives from a species of bulbous flowering plant in the genus *Allium*, See e.g., Garlic, Wikipedia, the free encyclopedia, last edited 29 Nov. 2021, herein incorporated by reference. The extract can be obtained by extraction. See Example 1. See also, e.g., Extraction (chemistry), Wikipedia, the free encyclopedia, last edited 25 Aug. 2021; and e.g., Natural Product (isolation and purification), Wikipedia, the free encyclopedia, last edited 8 Dec. 2021.

*Zingiber officinale* extract derives from a flowering plant in the family Zingiberaceae. See e.g., Ginger, Wikipedia, the free encyclopedia, last edited 25 Nov. 2021, herein incorporated by reference. The extracts can be obtained by extraction procedures. See Example 1 and "Analysis of Zinzirols in Kara Heart Formula by HPLC method", Green Chem, herein incorporated by reference (IDS). See also, e.g., Extraction (chemistry), Wikipedia, the free encyclopedia, last edited 25 Aug. 2021; and e.g., Natural Product (isolation and purification), Wikipedia, the free encyclopedia, last edited 8 Dec. 2021.

*Cinnamomum verum* extract derives from a small evergreen tree belonging to the family Lauraceae. See *Cinnamomum verum*, Wikipedia, the free encyclopedia, last edited 2 Nov. 2021, herein incorporated by reference. The extract can be obtained by extraction. See Example 1. See also, e.g., Extraction (chemistry), Wikipedia, the free encyclopedia, last edited 25 Aug. 2021; and e.g., Natural Product (isolation and purification), Wikipedia, the free encyclopedia, last edited 8 Dec. 2021.

The term 'hyperlipidemia' is a condition involving elevated levels of lipids in the blood. Hyperlipidemia generally includes elevated cholesterol levels in the blood. Elevated levels of lipids or cholesterol generally refers to amounts that exceed amounts considered normal according to standard medical practice. For example, high cholesterol can be defined as a total cholesterol level above 200 mg/dL. See Hyperlipidemia, Wikipedia, the free encyclopedia, last edited: 4 Oct. 2021, herein incorporated by reference.

Cholesterol is a type of lipid. See Cholesterol, Wikipedia, the free encyclopedia, last edited: 13 Oct. 2021, herein incorporated by reference.

The term 'therapeutically effective amount' refers to an amount of an active ingredient that produces the intended result, i.e., provides some level of treatment, modification, or has an effect on the condition of Hyperlipidemia in a mammal preferably a human. See e.g., Therapy, Wikipedia, the free encyclopedia, last edited 21 Nov. 2021, herein incorporated by reference.

The term 'administration' generally includes oral and intravenous administration as well as any route of administration capable of effectively delivering the composition to the body. Preferred would be pills or tablets. Administration may also be done through a food or beverage or through the skin or other body cavity. See Route of Administration, Wikipedia, the free encyclopedia, last edited 5 Nov. 2021, herein incorporated by reference.

KaraHeart™ is a synergistic herbal formula consisting of herbs including extract of *Commiphora mukul, Allium sativum, Camellia sinensis, Trigonella foenum*-graecum, *Zingiber officinale*, and *Cinnamomum verum*.

Dosage can be from about 100 mg to about 2000 mg per day. Preferred dosage is about 1000 mg per day.

Parameters for total cholesterol management include amounts of high-density lipoprotein (HDL), low-density lipoprotein (LDL), very-low-density lipoprotein (VLDL), and/or TGL (triglycerides) in the bloodstream.

Amounts of high-density lipoprotein (HDL), total cholesterol (TC), low density lipoprotein (LDL), very low density lipoprotein (VLDL), and/or triglycerides (TGL) in a mammal typically refers to measured amounts of these factors in the bloodstream of a mammal or human.

The term mammal as used herein are a group of vertebrate animals constituting the class Mammalia. See Mammal, Wikipedia, the free encyclopedia, last edited 18 Oct. 2021, herein incorporated by reference. Preferably mammal refers to primates and most preferably humans.

The term 'treatment' or 'treating' refers to the attempted remediation of a condition or health problem. Treatment can include providing relief to, preventing, curing, supporting, or maintaining a certain state with respect to a condition or management of a condition. Accordingly, treating hyperlipidemia can include prevention, management, e.g., halting or slowing the condition's development and effects, and relieving the symptoms of, as well as curing or eradicating the condition. See e.g., Therapy, Wikipedia, the free encyclopedia, last edited 21 Nov. 2021, herein incorporated by reference.

An active ingredient or active substance in a composition is an ingredient or substance that is biologically active. In embodiments, the compositions of the disclosure have more than one active ingredient. Excipients are generally biologically inactive ingredients, although need not necessarily be inert. See e.g., Active Ingredient, Wikipedia, the free encyclopedia, last edited 19 Oct. 2021, herein incorporated by reference.

An active ingredient of the *Commiphora mukul* extract comprises Commiphytes or Guggulsterone. See Guggulsterones, Wikipedia, the free encyclopedia, last edited 27 Jan. 2021, herein incorporated by reference.

An active ingredient of the *Camellia sinensis* extract comprises Camitechin or Epigallocatechin gallate. See Epigallocatechin gallate, Wikipedia, the free encyclopedia, last edited 16 Aug. 2021, herein incorporated by reference.

An active ingredient of the *Zingiber officinale* extract comprises Zinzirols or gingerols. See Gingerol, Wikipedia, the free encyclopedia, last edited 4 Oct. 2021, herein incorporated by reference.

A tablet or a pill is an oral dosage form that typically comprises a solid dosage with optional excipients. A tablet or a pill may also include liquids, syrups, elixirs, suspensions, and emulsions as well. See e.g., Tablet (pharmacy), Wikipedia, the free encyclopedia, last edited 21 Nov. 2021, herein incorporated by reference.

Percent amounts of extracts and active substances and other components of the claimed compositions are provided herein by weight.

Example 1

The Composition of KaraHeart™ Formula used in the Examples is as follows: *Commiphora mukul* extract, 30%; *Allium sativum* extract, 25%; *Camellia sinensis* extract, 15%; *Trigonella foenum*-graecum extract 15%; *Zingiber officinale* extract, 10%; *Cinnamomum verum* extract, 5%. All percentages are by weight. Specifications for each component are provided below.

Product name: *Allium sativum* extract; Botanical name: *Allium sativum*; Plant part: Bulbs; Excipients: Nil; Solvents used: Water.

| Test parameters | Specification | Testing method |
|---|---|---|
| Physical | | |
| Appearance | Light brown to brown powder | Visual |
| Identification (Identification using the WS of extract prepared using botanically authenticated Allium sativum bulbs) | To comply with working standard | In-house-HPTLC |
| Particle size | 98% min. passes through 20 mesh | USP |
| Loss on drying | NMT 6% | In-house-IR Moisture balance |
| Assay of actives | | |
| Saponins | NLT 6% | In-house-Gravimetry |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |

Product name: *Camellia sinensis* extract Botanical name: *Camellia sinensis*; Plant part: Leaves; Excipients: 5% Dextrin; Solvents used: Ethanol & Water.

| Test parameters | Specification | Testing method |
|---|---|---|
| Physical | | |
| Appearance | Brown to greenish brown powder | Visual |
| Identification (Identification using the WS of extract prepared using botanically authenticated Camellia sinensis leaves) | To comply with working standard | In-house-HPTLC |
| Particle size | 100% passes through 20 mesh | USP |
| Loss on drying | NMT 5% | In-house-IR Moisture balance |
| Assay of actives | | |
| Camitechin | NLT 40% | Based on USP-HPLC |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |
| Residual solvents | To comply with USP limits | USP |

Product name: *Cinnamomum verum* extract; Botanical name: *Cinnamomum verum* Plant part: Barks; Excipients: 5% Dextrin; Solvents used: Water.

| Test parameters | Specification | Testing method |
|---|---|---|
| Physical | | |
| Appearance | Brown powder with characteristic odour | Visual |
| Identification (Identification using the WS of extract prepared using botanically authenticated Cinnamomum verum barks) | To comply with working standard | In-house-HPTLC |
| Particle size | 98% min. passes through 20 mesh | USP |
| Loss on drying | NMT 10% | In-house-IR Moisture balance |
| Assay of actives | | |
| Polyphenols | NLT 3% | In-house-Titration |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |

Product name: *Commiphora mukul* extract; Botanical name: *Commiphora mukul* Plant part: Gum exudates; Excipients: 5% Dextrin; Solvents used: Ethanol & Water.

| Test parameters | Specification | Testing method |
| --- | --- | --- |
| Physical | | |
| Appearance | Cream colour powder | Visual |
| Identification (Identification using the WS of extract prepared using botanically authenticated Commiphora mukul gum exudates) | To comply with working standard | In-house-HPTLC |
| Particle size | 98% min. passes through 20 mesh | USP |
| Loss on drying | NMT 6% | In-house-IR Moisture balance |
| Assay of actives | | |
| Commiphytes | NLT 2.5% | In-house-HPLC |
| Microbial | | |
| Total plate count | NMT 1000 cfu/g | USP |
| Yeast and mold | NMT 100 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |
| Residual solvents | To comply with USP limits | USP |

Product name: *Trigonella foenum*-graecum extract; Botanical name: *Trigonella foenum*-graecum; Plant part used: Seeds; Solvents used: Water; Excipients: 5% Dextrin.

| Test parameters | Specification | Testing method |
| --- | --- | --- |
| Physical | | |
| Appearance | Brown to dark brown powder | Visual |
| Identification (Identification using the WS of extract prepared using botanically authenticated Trigonella (foenum-graecum seeds) | To comply with working standard | In-house-HPTLC |
| Particle size | 100% min. passes through 20 mesh | USP |
| Loss on drying | NMT 5% | In-house-IR Moisture balance |
| Assay of actives | | |
| Saponins | NLT 15% | In-house-Gravimetry |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |

Product name: *Zingiber officinale* extract; Botanical name: *Zingiber officinale*; Plant part: Roots (Rhizomes); Excipients: 5% Dextrin Solvents used: Ethanol & Water.

| Test parameters | Specification | Testing method |
| --- | --- | --- |
| Physical | | |
| Appearance | Brown to light brown powder | Visual |
| Identification (Identification using the WS of extract prepared using botanically authenticated Zingiber officinale roots) | To comply with working standard | In-house-HPTLC |
| Particle size | 98% min. passes through 20 mesh | USP |
| Loss on drying | NMT 10% | In-house-IR Moisture balance |
| Assay of actives | | |
| Zinzirols | NLT 5% | In-house-HPLC |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 3 ppm | USP-ICP-MS |
| Mercury | NMT 1 ppm | USP-ICP-MS |
| Pesticide residues | To comply with USP limits | USP |
| Residual solvents | To comply with USP limits | USP |

Product name: Kara Heart Formula. Blend of extracts of *Commiphora mukul, Allium sativum, Camellia sinensis, Trigonella foenum* graecum, *Zingiber officinale* and *Cinnamomum verum*.

| Test parameters | Specification | Testing method |
| --- | --- | --- |
| Physical | | |
| Appearance | Brown to reddish brown powder | Visual |
| Identification (Identification using the WS of extract prepared using botanically authenticated herbs) | To comply with working standard | In-house-HPTLC |
| Particle size | 100% min. passes through 20 mesh | USP |
| Loss on drying | NMT 5% | In-house-IR Moisture balance |
| Assay of actives | | |
| Commiphytes | NLT 0.75% | In-house-HPLC |
| Camitechin | NLT 6.0% | Based on USP-HPLC |
| Zinzirols | NLT 0.5% | In-house-HPLC |
| Microbial | | |
| Total plate count | NMT 1000 cfu/g | USP |
| Yeast and mold | NMT 100 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP-ICP-MS |
| Cadmium | NMT 1 ppm | USP-ICP-MS |
| Arsenic | NMT 1 ppm | USP-ICP-MS |
| Mercury | NMT 1 ppm | USP-ICP-MS |
| Pesticide residues | To comply with USP limits | USP |
| Residual solvents | To comply with USP limits | USP |

Example 2

Hyperlipidemia is a condition involving abnormally high levels of lipids in the blood. Hyperlipidemia is a major risk factor for cardiovascular diseases and refers to either high levels of triglycerides (TGL) or cholesterol. Herbal supplements have been used in the management of cholesterol levels in Ayurveda, a complete medical system originating in India. KaraHeart™ is a multi-herbal extract synergistic blend that may help in the management of healthy cholesterol levels. The current study tested the efficacy, tolerability, and safety of KaraHeart™ versus a placebo in the management of cholesterol levels of patients with mild to moderate hyperlipidemia.

This was a randomized, double-blind, parallel, and placebo-controlled study. A total of 100 patients were divided into two groups. One group was given KaraHeart™ and the other group was given a placebo for 120 days. Treatment results were assessed by checking the lipid profile parameters such as total cholesterol, high-density lipoprotein (HDL), low-density lipoprotein (LDL), very-low-density lipoprotein (VLDL), and TGL.

The study found that the herbal supplement KaraHeart™ significantly reduced levels of LDL, VLDL, TGL, and total cholesterol, while increasing the levels of HDL in the blood. Additionally, the study concluded that KaraHeart™ was safe to use.

KaraHeart™ was shown to be safe and effective in the management of cholesterol levels.

Hyperlipidemia is a common cause of morbidity worldwide. The most common form of hyperlipidemia is hypercholesterolemia (high cholesterol). High cholesterol is defined as a total cholesterol level above 200 mg/dL. Approximately one third of all ischemic heart diseases (IHDs) in the world are caused by hypercholesterolemia. Globally, as reported by the World Health Organization (WHO), increased cholesterol levels are estimated to cause 2.6 million deaths (4.5% of total) and 29.7 million (2% of total) disability adjusted life years (DALYs). In 2008, the worldwide prevalence of hypercholesterolemia in western countries among adults was 39% in males and 40% in females.

Hyperlipidemia is defined under the umbrella of dyslipidemia, a metabolic abnormality leading to an increase in the plasma concentration of cholesterol and/or triglycerides. These disorders occur due to the elevation of serum cholesterol (total cholesterol/TC), low-density lipoprotein (LDL-C), very-low-density lipoprotein (VLDL), or triglyceride (TGL) concentrations, and a decrease in high-density lipoprotein (HDL-C) cholesterol concentrations. In general, HDL is considered "good cholesterol" while LDL, VLDL and TGL, are considered "bad cholesterol". The ratios of TC/HDL-C and LDL-C/HDL-C are used for predicting the risk of developing ischemic heart disease (IHD).

Typically, the higher the levels of lipids in the blood, the higher the risk of cardiovascular diseases (CVD).

Hyperlipidemia is classified into primary and secondary forms. Primary hyperlipidemia is usually hereditary with a genetic cause, while secondary hyperlipidemia is usually caused by other underlying diseases, dietary factors and/or medications/drugs. Though hyperlipidemia itself does not cause any symptoms, it can lead to symptomatic vascular diseases such as coronary artery disease (CAD), stroke, and peripheral arterial disease (PAD). The impact of cholesterol can be reduced by proper management of hyperlipidemia through lifestyle changes and medications. Concerns about adverse reactions to medications for hyperlipidemia, coupled with high costs, may hinder the long-term use of conventional medicines. Use of alternative treatments and natural supplements may reduce such treatment burden and may help to better and more safely manage hyperlipidemia in the general population.

The following study was conducted to test the efficacy, tolerability, and safety of KaraHeart™ in managing cholesterol levels as compared to a placebo control.

Methods

This was a randomized, double-blind, placebo-controlled study. Reporting of the study was done according to Consolidated Reporting of Randomized Controlled Trials (CONSORT) guidelines.

The study was performed in accordance with the current version of the Declaration of Helsinki. The trial was conducted in agreement with the International Conference on Harmonization (ICH) guidelines on Good Clinical Practice (GCP) and the applicable rules and regulations of India.

The study was performed under strict compliance with the requirements of Indian regulations for carrying out the herbal and Ayurveda clinical trials and Ayurveda, Siddha, and Unani good clinical practices (ASU-GCP). ICH guidelines for Good Clinical Practice (ICH-GCP) issued by the U.S. Department of Health and Human Services were followed wherever applicable. Informed consent was obtained from all participants. The trial was registered with Clinical Trials Registry (CTRI), hosted at the ICMR's National Institute of Medical Statistics as per the mandate of Drugs Controller General of India (DCGI). The trial was also registered with the World Health Organization.

Participants

Sample size was calculated using analysis of covariance (ANCOVA) using the primary objectives. The number of measures pre-randomization and post-randomization were 1 and 4 respectively, assuming an anticipated standard effect size of 0.4 and interclass correlation of 0.5. Estimating a drop-out rate of approximately 25%, a minimum of 47 patients in each arm were needed to be recruited to obtain a power rate of more than 80%. Hence a total of 100 participants, 50 in each arm were recruited in the study.

Inclusion Criteria

Healthy adult men and women between the ages of 20-60 years with a confirmed case of mild to moderate hyperlipidemia As per ATP III guidelines; baseline LDL ranging >100 mg/dL, TC>200 mg/dL, TGL between 150-199 mg/dL, VLDL-Cholesterol >40 mg/dL, HDL-cholesterol: Men-<40 mg/dL, and women <50 mg/dL Subjects with at least one or more of the diagnostic criteria mentioned above were selected for the study Subjects with Normal BMI but Abnormal Lipid Profile Subjects who were able to understand the risks/benefits of the protocol and were willing to give written informed consent Exclusion Criteria Subjects who: were using concurrent lipid-lowering medications like statins or fibrates, or dietary supplements within 30 days prior to screening; had hyperlipidemia due to other medications (e.g. Glucocorticoids); had chronic diseases requiring continuous use of vasoactive diuretics or lipid-lowering drugs; were intractably obese or who had experienced any recent, unexplained weight loss or gain; had a history of major illness or cardiovascular diseases (e.g. Angina pectoris, myocardial infarction, etc.) or a history of a thyroid disorder (TSH-levels of <0.4 or >10 µg/dL), renal disorder, cholelithiasis, polycystic ovary syndrome (PCOS), Type I or II diabetes, abnormal liver or kidney function test (ALT or AST) two times the upper limit of normal or elevated creatinine (male 125 μmol/L, female 110 μmol/L), a positive HIV test, a history of smoking and/or high alcohol intake (2 standard drinks per day); a history of psychiatric disorders that may impair the ability of subjects to provide written informed consent; females who were pregnant, breast feeding, or planning to become pregnant during the study. Also excluded, were subjects with any other condition that, in the opinion of investigator, would adversely affect the subject's ability to complete the study or its measures.

Finally, subjects with a known allergy to KaraHeart™ constituents or ingredients were also excluded from the study Intervention KaraHeart™ is a synergistic herbal formula consisting of herbs, such as extract of *Commiphora mukul, Allium sativum, Camellia sinensis, Trigonella foenum*-graecum, *Zingiber officinale,* and *Cinnamomum verum.*

Both KaraHeart™ and placebo were in the form of 500 mg capsules. Daily dosage for both products was 1000 mg (i.e. 2 capsules/day).

Trial Design

A total of 122 subjects were screened for a final sample size of 100 randomized subjects. Eligible subjects were randomly allocated to either of the study arms in accordance with the randomization code found on the study product containers' label. The same was documented into the randomization record. Identical and sealed packed bottles of KaraHeart™ and placebo capsules were provided to the clinical sites. Investigators prescribed the allocated number of bottles of either KaraHeart™ or placebo in a blinded manner to the subjects on a first come, first served basis.

A total of 100 subjects (50 subjects in each arm) were recruited randomly into the two study arms: Group A—KaraHeart™ and Group B—placebo. Duration of the study was 120 days with 6 scheduled clinical visits (screening visit, baseline, 30 days, 60 days, 90 days, and 120 days). Each visit had a window period of ±3 days (FIG. 1).

Subjects were given assigned medication at visit 2 (day 1) and asked to take 1 capsule orally, twice daily (after breakfast and dinner). Subjects were given supplements to last until the next visit (visit 3, day 30±3) and asked to record daily consumption in the diaries and compliance cards provided to them. Subjects were also asked to walk for 30 minutes daily and record adverse events, if any. With the exception of the biostatistician, all others (the sponsor's designee, investigator, subjects, and CRO's designee) were kept blinded to the investigational product (IP) provided to each participant. Similarly, all others (the sponsor's designee, investigator, subjects and CRO's designee) were kept blinded about the Investigational Product (IP) provided to each participant. The screening visit included obtaining the informed consent, demographic details of the participants, physical examination, recording of vital signs, collecting medical history from the patients, and laboratory examinations. Height, weight, and BMI of subjects were recorded during the screening visit. Each subject underwent clinical laboratory tests at screening and follow-up visits. Urine for urinalysis and blood for hematology, biochemistry, and serology were collected during screening and at the end of the study visit. For the hematology, biochemistry, and serology laboratory tests, blood samples were collected by direct venipuncture of peripheral veins for clinical laboratory tests at the screening visit (V1), follow-up visits, and the final visit (V6). A total of approximately 40 to 45 ml of blood was collected over the course of this study for clinical laboratory evaluations. Blood and urine samples were collected from each prospective participant to analyze and assess the inclusion criteria for fasting/random blood sugar (FBS/RBS), HbA1C, C-Reactive Protein, ECGs, HIV, liver function tests, kidney/renal function tests and urinalysis were performed during the course of the study. In all female subjects of child-bearing potential, a urine pregnancy test was performed during visits V1-6. Negative results were recorded in the source document to confirm the non-pregnant status of participants in order to confirm eligibility for enrolment and/or continuation in the study.

Each follow-up visit (days 30, 60, 90, and 120±3) involved distribution of the supplement, assessments of lipid parameters, and collection of safety and tolerability information. At no point was the code broken, or un-blinded study product administered to any subject. The investigator had the right to break the blind in special situations such as for treatment of emergent serious adverse events (SAE) or to protect the safety of the patient, but it was not necessary for any participant over the duration of the study.

Compliance and Adverse Events

Any unused or extra medication was returned to the investigators to confirm that the correct number of capsules had been taken. The investigator verified the subjects' daily diary and compliance cards and reconciled the supplement use to subjects. This reconciliation was logged on the IP reconciliation form. Proper care was made to record all adverse events (AEs) in source documents and case report forms (CRF).

AE were recorded for severity and relationship to the consumption of the study supplement. All AEs were followed until they were resolved or stabilized or until they were no longer considered clinically significant by the investigator. All reported AEs were mild to moderate in nature, thus, no additional measurements or evaluations were done to investigate the nature of an AE. There were no severe AEs (SAEs) reported during the study.

Withdrawal and Dropout

Subjects who did not meet inclusion/exclusion criteria were considered screen failures.

Participating subjects could withdraw at any time without the need to justify his/her decision, even after undergoing consenting process (consent withdrawal). No subject was discontinued from the study due to non-compliance with medication, protocol violation, worsening of disease or tolerability, AEs, or SAEs. A total of five subjects (from treatment and placebo groups) dropped out from the study at different intervals due to personal reasons. None of these subjects dropped out due to any AE. Data from these subjects were used to examine safety, but not efficacy. The withdrawal of these subjects was prior to the final outcome assessments; therefore, their data was excluded from the main analysis. In case of statistics on the ITT population, missing values were replaced using the last observation carried forward (LOCF) method and efficacy assessments were completed.

Outcome Measures

Primary outcome measures: Change in the following lipid profile parameters from baseline to end of treatment period at the following time points: Baseline, Day 30 (±3), Day 60 (±3), Day 90 (±3) and Day 120 (±3).

Total Cholesterol (TC): This is a sum of the blood cholesterol content. The average level of TC should be below 200 mg/dL.

High-Density Lipoprotein (HDL): This is called "good" cholesterol because it helps carry away LDL, thus keeping arteries open and blood flowing more freely. The average level of HDL should be above 40 mg/dL.

Low-Density Lipoprotein (LDL): This is called "bad" cholesterol. Too much of it in your blood causes a build-up of fatty deposits (plaques) in the arteries (atherosclerosis), which reduces blood flow. These plaques sometimes rupture and can lead to a heart attack or stroke. The average level of LDL should be less than 100 mg/dL.

Triglycerides (TGL): Triglycerides are a type of fat in the blood. The body converts calories it doesn't need into triglycerides, which are stored in fat cells. High triglyceride levels are associated with being overweight, eating sweets or drinking too much alcohol, smoking, sedentary lifestyle, or diabetes with elevated blood sugar levels. The average levels of triglycerides should be less than 150 mg/dL.

Very-Low-Density Lipoprotein (VLDL): The liver makes VLDL and releases it into the bloodstream. VLDL particles mainly carry triglycerides to the tissues. Elevated levels of VLDL can increase a person's risk of developing heart diseases. Normal VLDL should be less than 30 mg/dL.

Total HDL-Cholesterol Ratio: The ratio of TC/HDL. The optimal ratio is between 3.5 and 1. A higher ratio indicates an increased risk of heart disease.

Secondary Outcome Measures:

Change from Baseline to end of study period (Day 120) in:

Serum Apolipoprotein A1: Apolipoproteins are proteins that bind lipids together to form lipoproteins. Their main function is transportation of lipids (and fat-soluble vitamins) in blood, cerebrospinal fluid, and lymph fluid. The 2 major apolipoproteins responsible for lipid transport are ApoA1 and ApoB. Decreases in the concentration of ApoA1 levels along with increases in the concentration of ApoB are associated with increased risk of cardiac diseases. The ApoA1 is the major protein component of HDL and is associated with fat efflux from tissue to liver for excretion. In patients suffering from CAD, ApoA1 levels serve as a better diagnostic tool than HDL levels as they have higher sensitivity and specificity.

HbA1C: To control and monitor the glycemic index in diabetic patients, the HbA1C test is routinely performed. Factors such as sugar intake, exercise, and adherence to medications can affect the levels of HbA1C. Studies have reported that HbA1c can be utilized as a possible biomarker for predicting dyslipidemia and cardiovascular diseases (CVD). A study published in 2017 found that the ideal HbA1c level for people without diabetes is in the 5.0% to 6.0% range. Beyond 6.0%, the risk of death from CVDs rises significantly.

C-reactive protein (CRP): CRP is an inflammatory marker. Inflammation is a major factor in any atherothrombotic disease. Levels of high-sensitivity C-reactive protein (hs-CRP), a marker of systemic inflammation and a mediator of atherothrombotic disease, are potential risk factors for cardiovascular disease. Currently, CRP is recognized as an indicator of vascular inflammation. CRP may be used as a predictor of cardiovascular conditions secondary to atherosclerosis and is a strong predictor of cardiovascular events when compared with low-density lipoprotein cholesterol (LDL-C). The evaluation of serum CRP together with the lipid pattern can be very useful in the early identification of type 2 diabetic individuals who are at high risk of developing CVD.

Statistical Analysis:

Study data collected was assessed using Statistical Analysis Software (SAS) 9.4 package. Descriptive analysis for baseline summary statistics, including mean, medians, and standard deviation for demographic data and proportion of males and females was performed.

The intention to treat (ITT) efficacy analysis set consisted of subjects who took at least 1 dose of IP and have at least 1 post-baseline assessment. ITT efficacy analysis was provided only for the primary end point. Per protocol set population (PP) analysis set was a subset of the ITT population, consisting of subjects who had no major protocol violations affecting the primary efficacy variables. A total of 95 subjects completed the study and were included in the PP population analysis.

Data are expressed as mean±standard deviation (SD). P values were calculated using paired Students t-tests to compare time points within the same group, ANOVA was performed to compare groups at same time point, or ANCOVA using baseline measurement as a covariant when comparing baseline to V6 across groups. Missing post-baseline observations were imputed using last observation carried forward approach (LOCF). All hypotheses were tested at a significance level of 0.05 and 95% confidence interval.

Results

In total, five subjects discontinued the study: one dropped out in V4 from the placebo group, two subjects dropped out in V5 from the treatment (KaraHeart™) group and two subjects dropped out in V6 from the placebo group; these subjects were included in data analysis as ITT population through LOCF method. However, all efficacy analysis were performed using PP population (Table 1). A summary of baseline demographic data of subjects is summarized in Table 2.

Statistical analysis of Total Cholesterol (TC) (PP Population) revealed that at baseline there were no significant differences in the values between the KaraHeart™ and placebo groups (P>0.05). An independent Students t-test was performed (Table 3) and was non-significant (P=0.8935) at baseline, confirming that the total cholesterol at baseline between the groups were essentially identical at the beginning of the study and thus, results at the end of study were comparable. ANCOVA was performed to test different effects by eliminating unwanted variance on the outcome variable. ANCOVA analysis did not show a difference at Day 30 between the groups (P>0.05). However, TC in KaraHeart™ group was significantly different at Day 30 as compared to baseline (P<0.0001), unlike the placebo group. These results suggest that KaraHeart™ helped reduce TC within 30 days of treatment. KaraHeart™ continued to show statistically significant reductions in the level of TC when compared to baseline at Day 60 (5%; ANCOVA P=0.0022), Day 90 (7.9%; ANCOVA P=0.0213) and Day 120 (10.5%; ANCOVA P=0.0397) when compared to the placebo group. By Day 120, the KaraHeart™ group demonstrated approximately twice the reduction in TC compared to that of the placebo group. The placebo group did not show any statistically significant improvement until Day 90, whereas the KaraHeart™ group began showing statistically significant decreases in TC starting at Day 30 (Table 3).

The HDL level was well maintained in the KaraHeart™ group with no statistical difference observed at Day 30 from Baseline. In contrast, the placebo group demonstrated a statistically significant reduction in HDL. At Day 120, the KaraHeart™ group had a statistically significant increase in HDL of 4.7% whereas the placebo group showed a statistically significant decrease in HDL of 5.32%. These data indicate that, without active treatment, the patients' HDL levels were deteriorating (Table 4A). The ANCOVA P values were significant at all time points (Days 30, 60, 90, and 120) indicating that KaraHeart™ increased HDL levels. In a sub-group analysis of high-risk category patients (baseline HDL below 40 mg/dl), HDL levels in the KaraHeart™ treated group demonstrated an even greater increase than the entire KaraHeart™ group in HDL compared to the placebo group. In this sub-group analysis (Table 4B), a significant increase of HDL (4.67 mg/dl, 13.27%) was observed in the KaraHeart™ group from the baseline to the end of study indicating that KaraHeart™ improved HDL levels. In contrast, there was a decrease of 0.9 mg/dl (2.7%) observed in the placebo group (sub-group analysis) from baseline to the end of study. The ANCOVA P value (0.0089) is significant in the sub-group analysis of HDL levels indicating that KaraHeart™ is effective at increasing HDL, whereas the placebo group experienced deteriorating HDL levels. The paired Students t-test (P=0.004) was significant for KaraHeart™ group, but not for the placebo group (P=0.5355) indicating that that treatment group improved significantly from baseline, but the placebo group did not.

At day 120, the KaraHeart™ group had a tendency toward a decrease in LDL compared to the placebo group, as demonstrated by a nearly 13 mg/dL decrease in mean LDL level compared (10% decrease) to the placebo group (approximately 3 mg/dl increase in mean LDL, a 2.3% increase) ANCOVA P=0.095) (Table 5).

The KaraHeart™ group had a statistically significant reduction in VLDL levels, as compared to baseline, from Day 30 through Day 120. The KaraHeart™ group had statistically significant reductions in mean VLDL of 3 mg/dL (9% reduction) and 7 mg/dL (20% reduction) at Day 30 and Day 120, respectively. In contrast, there was no statistically significant reduction observed in VLDL in the placebo group at any time point compared to baseline. ANCOVA P-values for days 30, 60, 90, and 120 were all less than 0.05 (Table 6A). In a sub-group analysis of high-risk patients (Baseline VLDL above 40 mg/dl), there was a significant decrease (P<0.0001) of 16.3 mg/dl (33.28%) observed indicating a positive effect of KaraHeart™. There was no statistically significant change (P>0.05) observed in the level of VLDL in placebo group from baseline to the end of the study. The ANCOVA p value was significant (p=0.0020), which was due to reduction of VLDL in KaraHeart™ group (Table 6B).

The KaraHeart™ group had a statistically significant reduction of mean TC/HDL-C at Day 30 (5% decrease), Day 60 (8% decrease), Day 90 (11% decrease), and Day 120 (15% decrease) compared to baseline. The placebo group showed no statistically significant decrease during any of the time point.

ANCOVA P-values were less than 0.05 at all measurement times (Table 7).

The KaraHeart™ group had a statistically significant reduction in triglycerides at all time points compared to baseline, whereas the placebo group had no significant reduction at any time point. At Day 30, the KaraHeart™ group had a mean 15.3 mg/dL unit decrease (9% decrease), and by Day 120, the group had nearly a 37 mg/dL decrease (21% decrease) of triglycerides. ANCOVA P-values were less than 0.05 at all measurement times (Table 8A). In a sub-group analysis of high-risk category patients (baseline triglycerides above 160 mg/dl), the KaraHeart™ had an even greater decrease in triglycerides at all time points compared to baseline with a decrease of 81.5 mg/dl (33.2%) in KaraHeart™ group from the baseline to the end of the study period. In contrast, the placebo group did not have a statistically significant change in triglycerides from baseline to end of study in the high-risk sub-group (p=0.0858). ANCOVA P-value (0.0020) and P-value between the two groups (0.0001) were significant indicating that KaraHeart™ was more effective at reducing triglyceride level than the placebo. In the category of patients with baseline TGL values between 160 to 200 mg/dl, a decrease of 38.6 mg/dl.

(22%) was observed in the KaraHeart™ group and a negligible non-statistically significant decrease of 1.9 mg/dl (1.1%) was observed in the placebo group from baseline to the end of the study. The ANCOVA P-value was significant (0.0361) indicating a difference between the groups and supporting a role for KaraHeart™ in decreasing triglycerides in the blood. (Table 8B)

Average HbA1C at baseline in the KaraHeart™ group was 5.37 (SD=0.349) and was 5.42

(SD=0.410) in the placebo group. The mean of two groups was statistically comparable (P=0.536) at Day 0. The level of HbA1C increased 0.17 units from baseline to Day 120 in the KaraHeart™ group (P<0.0001) and it increased by 0.24 units in the placebo group (P<0.0001). ANCOVA P-value was 0.2633 (Table 9A).

Mean C-reactive protein (CRP) in the KaraHeart™ group was 6.54 (SD=1.518) mg/L and mean CRP in the placebo group was 6.22 (SD=1.278) mg/L at the Baseline visit. CRP decreased by 0.59 units at Day 120 from Baseline in KaraHeart™ group (P=0.0463) and decreased by 0.07 units in placebo group (P=0.7717). ANCOVA p-value was 0.4160 (Table 9A).

Serum Apolipoprotein A1 (ApoA1) in the KaraHeart™ group was 136.81 mg/dL (SD=23.237) and in placebo group was 138.81 mg/dL (SD=26.285) at the Baseline visit. In the KaraHeart™ group, ApoA1 increased by 5.37 units at Day 120 compared to Baseline (p=0.0122) and decreased by 1.37 units in the placebo group (P=0.6678). The ANCOVA P-value at Day 120 was 0.0893 (Table 9A). The normal range of ApoA1 for men is 110-180 mg/dL and 250 mg/dL for women. High levels of ApoA1 is considered beneficial for cardiac health and can be considered independently of HDL levels.

KaraHeart™ increased the ApoA1 levels in the present study suggesting that it is beneficial for cardiac health. Table 9B indicates that the subgroup analysis (high, moderate, and low levels of ApoA1) did not reveal any statistically significant differences.

Adverse Events

There were no serious adverse events observed in this study. KaraHeart™ was well tolerated with few mild to moderate side effects which were equally distributed between the KaraHeart™ and placebo groups (3 cases in the KaraHeart™ group, 4 cases in placebo group) (Table 10).

DISCUSSION

The therapeutic goal for treating hyperlipidemia and associated CVD is to manage the level of cholesterol in the blood. Cholesterol is managed by increasing HDL and decreasing LDL, VLDL, and TGL in the blood. In the present study, we show that KaraHeart™ (a supplement with a proprietary herbal composition) is safe and effective in treating hyperlipidemia. Supplementation with KaraHeart™ increased HDL and reduced the levels of LDL, VLDL, TGL and TC in the blood. This study also showed that supplementation with 1000 mg/day of KaraHeart™ was safe, as there were no serious adverse side effects. Thus, KaraHeart™ is shown to be safe and effective in helping patients manage their cholesterol levels.

In conclusion, this study demonstrated that KaraHeart™, a synergistic herbal extract blend, helped manage cholesterol levels by normalizing lipid parameters. KaraHeart™ did not alter the vital signs of the patients and did not cause any serious adverse side effects, making it a safe and effective treatment option for patients with mild to moderate hyperlipidemia.

TABLE 1

Analysis of data sets.

| Study Population | n KaraHeart ™ | n Placebo |
|---|---|---|
| Total number of subjects screened | 122 | |
| Total number of subjects enrolled & randomized (V2) (Day 0) | 50 | 50 |
| Drop-out at visit V3 (Day 30 ± 3) | 0 | 0 |
| Drop-out at visit V4 (Day 60 ± 3) | 1 | 0 |
| Drop-out at visit V5 (Day 90 ± 3) | 2 | 0 |
| Drop-out at visit V6 (Day 120 ± 3) | 0 | 2 |
| Intent-to-Treat (ITT) Population | 50 | 50 |
| Safety Population | 50 | 50 |
| Per-Protocol (PP) Population | 47 | 48 |

TABLE 2

Statistical summary for subjects' demography.

| Name | Statistics | KaraHeart ™ (N = 50) | Placebo (N = 50) | P-Value |
|---|---|---|---|---|
| Gender | | | | |
| Female | n (%) | 26 (52.0%) | 24 (48.0%) | |
| Male | n (%) | 24 (48.0%) | 26 (52.0%) | |
| Age (Year) | n | 50 | 50 | .3044 |
| | Mean (SD) | 40.80 (9.413) | 38.84 (9.571) | |
| | Median | 39.5 | 38.0 | |
| | (Min, Max) | (20.00, 60.00) | (21.00, 60.00) | |
| Height (m) | n | 50 | 50 | .0547 |
| | Mean (SD) | 1.61 (0.090) | 1.64 (0.077) | |
| | Median | 1.6 | 1.7 | |
| | (Min, Max) | (1.45, 1.80) | (1.46, 1.82) | |
| Weight at Day 0 (kg) | n | 50 | 50 | .4184 |
| | Mean (SD) | 65.89 (9.893) | 67.32 (7.660) | |
| | Median | 63.5 | 67.0 | |
| | (Min, Max) | (43.00, 93.10) | (54.00, 83.00) | |
| Weight at Day 30 (kg) | n | 50 | 50 | |
| | Mean (SD) | 65.65 (9.778) | 66.96 (7.783) | |
| | Median | 63.5 | 66.0 | |
| | (Min, Max) | (43.00, 93.10) | (54.00, 83.00) | |
| Weight at Day 60 (kg) | n | 49 | 50 | |
| | Mean (SD) | 65.66 (9.716) | 66.92 (7.793) | |
| | Median | 63.0 | 66.0 | |
| | (Min, Max) | (43.00, 93.10) | (54.00, 83.00) | |
| Weight at Day 90 (kg) | n | 47 | 50 | |
| | Mean (SD) | 65.22 (9.970) | 66.68 (7.686) | |
| | Median | 63.0 | 65.9 | |
| | (Min, Max) | (43.00, 93.10) | (54.00, 83.00) | |
| Weight at Day 120 (kg) | n | 47 | 48 | |
| | Mean (SD) | 63.96 (9.809) | 66.91 (7.586) | |
| | Median | 62.0 | 66.4 | |
| | (Min, Max) | (43.00, 89.00) | (55.00, 83.00) | |
| BMI at Day 0 ($kg/m^2$) | n | 50 | 50 | .4112 |
| | Mean (SD) | 25.28 (2.490) | 24.89 (2.241) | |
| | Median | 25.3 | 24.6 | |
| | (Min, Max) | (19.11, 30.44) | (20.06, 29.75) | |
| BMI at Day 30 ($kg/m^2$) | n | 50 | 50 | |
| | Mean (SD) | 25.19 (2.481) | 24.75 (2.288) | |
| | Median | 25.3 | 24.3 | |
| | (Min, Max) | (19.11, 30.44) | (19.75, 29.75) | |
| BMI at Day 60 ($kg/m^2$) | n | 49 | 50 | |
| | Mean (SD) | 25.17 (2.484) | 24.74 (2.338) | |
| | Median | 25.4 | 24.4 | |
| | (Min, Max) | (19.11, 30.44) | (19.75, 30.12) | |
| BMI at Day 90 ($kg/m^2$) | n | 47 | 50 | |
| | Mean (SD) | 25.04 (2.577) | 24.65 (2.265) | |
| | Median | 25.1 | 24.4 | |
| | (Min, Max) | (19.11, 30.44) | (19.75, 29.75) | |
| BMI at Day 120 ($kg/m^2$) | n | 47 | 48 | |
| | Mean (SD) | 24.55 (2.481) | 24.68 (2.310) | |
| | Median | 23.9 | 24.4 | |
| | (Min, Max) | (19.11, 29.69) | (19.75, 29.75) | |

Note:
P Value: Two sample t-test

TABLE 3

Statistical analysis for Total Cholesterol (TC) (Per protocol population)

| Variable | KaraHeart ™ (N = 47) | Placebo (N = 48) | P-Value[a] | ANCOVA P-Value[c] |
|---|---|---|---|---|
| TC at Day 0 (mg/dl) | 206.3 (33.026) | 207.1 (25.004) | .8935 | .1435 |
| TC at Day 30 (mg/dl) | 201.1 (31.719) | 204.6 (22.979) | .5405 | |
| Mean Difference | −5.26 | −2.56 | | |
| CI | (−7.434, −3.077) | (−5.882, 0.757) | | |
| P-value[b] | <.0001 | .1271 | | |
| TC at Day 0 (mg/dl) | 206.3 (33.026) | 207.1 (25.004) | .8935 | .0022 |
| TC at Day 60 (mg/dl) | 195.9 (29.829) | 206.3 (23.195) | .0617 | |
| Mean Difference | −10.4 | −0.85 | | |
| CI | (−14.55, −6.260) | (−6.287, 4.579) | | |
| P-value[b] | <.0001 | .7532 | | |
| TC at Day 0 (mg/dl) | 206.3 (33.026) | 207.1 (25.004) | .8935 | .0213 |
| TC at Day 90 (mg/dl) | 190.1 (29.109) | 199.9 (25.887) | .0878 | |
| Mean Difference | −16.2 | −7.25 | | |
| CI | (−22.11, −10.27) | (−13.70, −0.803) | | |
| P-value[b] | <.0001 | .0283 | | |
| TC at Day 0 (mg/dl) | 206.3 (33.026) | 207.1 (25.004) | .8935 | .0397 |
| TC at Day 120 (mg/dl) | 184.7 (30.446) | 195.7 (30.743) | .0812 | |

TABLE 3-continued

Statistical analysis for Total Cholesterol (TC) (Per protocol population)

| Variable | KaraHeart ™ (N = 47) | Placebo (N = 48) | P-Value[a] | ANCOVA P-Value[c] |
|---|---|---|---|---|
| Mean Difference | −21.7 | −11.4 | | |
| CI | (−29.50, −13.82) | (−19.25, −3.540) | | |
| P-value[b] | <.0001 | .0054 | | |

Note:
P Value[a]: Two sample t-test.
P value[b]: Paired t-test.
P Value[c]: ANCOVA P Value.

TABLE 4A

Statistical Analysis for High Density Lipoprotein-Cholesterol (HDL-C) (Per Protocol Population)

| Variable | KaraHeart ™ (N = 47) | Placebo (N = 48) | P-Value[a] | ANCOVA P-Value[c] |
|---|---|---|---|---|
| HDL-C at Day 0 (mg/dl) | 43.15 (8.715) | 43.38 (10.342) | .9086 | .0074 |
| HDL-C at Day 30 (mg/dl) | 43.81 (7.459) | 41.56 (10.683) | .2373 | |
| Mean Difference | 0.66 | −1.81 | | |
| CI | (−0.339, 1.659) | (−3.390, −0.235) | | |
| P-value[b] | .1904 | .0252 | | |
| HDL-C at Day 0 (mg/dl) | 43.15 (8.715) | 43.38 (10.342) | .9086 | .0001 |
| HDL-C at Day 60 (mg/dl) | 44.23 (7.429) | 40.92 (10.465) | .0779 | |
| Mean Difference | 1.09 | −2.46 | | |
| CI | (−0.017, 2.187) | (−3.943, −0.974) | | |
| P-value[b] | .0534 | .0017 | | |
| HDL-C at Day 0 (mg/dl) | 43.15 (8.715) | 43.38 (10.342) | .9086 | .0004 |
| HDL-C at Day 90 (mg/dl) | 44.45 (7.762) | 40.56 (10.320) | .0412 | |
| Mean Difference | 1.30 | −2.81 | | |
| CI | (−0.054, 2.650) | (−4.755, −0.870) | | |
| P-value[b] | .0596 | .0055 | | |
| HDL-C at Day 0 (mg/dl) | 43.15 (8.715) | 43.38 (10.342) | .9086 | .0005 |
| HDL-C at Day 120 (mg/dl) | 45.17 (7.707) | 41.06 (10.873) | .0363 | |
| Mean Difference | 2.02 | −2.31 | | |
| CI | (0.472, 3.571) | (−4.281, −0.344) | | |
| P-value[b] | .0117 | .0223 | | |

Note:
P Value[a]: Two sample t-test.
P value[b]: Paired t-test
P Value[c]: ANCOVA P Value.

TABLE 4B

Sub-Group Analysis:

| CATEGORY | Variable | KaraHeart ™ Group (N = 47) | Placebo Group (N = 48) | P-Value[a] | ANCOVA P-Value[c] |
|---|---|---|---|---|---|
| HDL Above 45 mg/dl | N | 15 | 18 | | |
| | BASELINE | 53.13 (6.435) | 53.67 (9.299) | .7115 | .3369 |
| | V6 | 51.80 (8.117) | 50.33 (9.804) | .6477 | |
| | Mean Difference | −1.33 | −3.33 | | |
| | CI | (−3.565, 0.898) | (−7.483, 0.817) | | |
| | P-value[b] | .2208 | .1084 | | |
| HDL 40 to 45 mg/dl | N | 14 | 11 | | |
| | BASELINE | 42.71 (1.541) | 41.91 (1.514) | .3103 | .0033 |
| | V6 | 44.93 (3.731) | 38.91 (4.085) | .0015 | |
| | Mean Difference | 2.21 | −3.00 | | |
| | CI | (0.238, 4.191) | (−5.585, −0.415) | | |
| | P-value[b] | .0309 | .0271 | | |

TABLE 4B-continued

Sub-Group Analysis:

| CATEGORY | Variable | KaraHeart ™ Group (N = 47) | Placebo Group (N = 48) | P-Value[a] | ANCOVA P-Value[c] |
|---|---|---|---|---|---|
| HDL Below 40 mg/dl | N | 18 | 19 | | |
| | BASELINE | 35.17 (3.746) | 34.47 (2.342) | .5018 | .0089 |
| | V6 | 39.83 (5.182) | 33.53 (7.741) | .0065 | |
| | Mean Difference | 4.67 | −0.95 | | |
| | CI | (1.698, 7.636) | (−4.098, 2.203) | | |
| | P-value[b] | .0041 | .5355 | | |

Note:
P Value[a]: Two sample t-test.
P Value[b]: Paired t-test
P Value[c]: ANCOVA P Value.

TABLE 5

Statistical Analysis for Low Density Lipoprotein-Cholesterol (LDL-C) (Per Protocol Population)

| Variable | KaraHeart ™ (N = 47) | Placebo (N = 48) | P-Value[a] | ANCOVA P-Value[c] |
|---|---|---|---|---|
| LDL-C at day 0 (mg/dl) | 124.8 (28.912) | 120.6 (23.005) | .4345 | .5277 |
| LDL-C at day 30 (mg/dl) | 126.1 (27.902) | 125.7 (24.644) | .9414 | |
| Mean Difference | 1.27 | 5.07 | | |
| CI | (−5.126, 7.656) | (−0.652, 10.792) | | |
| P-value[b] | .6921 | .0811 | | |
| LDL-C at day 0 (mg/dl) | 124.8 (28.912) | 120.6 (23.005) | .4345 | .0979 |
| LDL-C at day 60 (mg/dl) | 123.5 (26.180) | 128.3 (24.723) | .3649 | |
| Mean Difference | 1.35 | 7.61 | | |
| CI | (−7.797, 5.102) | (0.370, 14.854) | | |
| P-value[b] | .6760 | .0398 | | |
| LDL-C at day 0 (mg/dl) | 124.8 (28.912) | 120.6 (23.005) | .4345 | .2221 |
| LDL-C at day 90 (mg/dl) | 118.7 (26.606) | 122.2 (27.437) | .5378 | |
| Mean Difference | −6.11 | 1.52 | | |
| CI | (−13.00, 0.784) | (−6.395, 9.444) | | |
| P-value[b] | .0810 | .7003 | | |
| LDL-C at day 0 (mg/dl) | 124.8 (28.912) | 120.6 (23.005) | .4345 | .0095 |
| LDL-C at day 120 (mg/dl) | 112.3 (28.107) | 123.4 (26.663) | .0504 | |
| Mean Difference | −12.6 | 2.79 | | |
| CI | (−20.00, −5.108) | (−5.751, 11.334) | | |
| P-value[b] | .0014 | .5141 | | |

Note:
P Value[a]: Two sample t-test.
P value[b]: Paired t-test
P Value[c]: ANCOVA P Value.

45

TABLE 6A

Statistical Analysis for Very Low Density Lipoprotein-Cholesterol (VLDL-C) (Per Protocol Population)

| Variable | KaraHeart ™ (N = 47) | Placebo (N = 48) | P-Value[a] | ANCOVA P-Value[c] |
|---|---|---|---|---|
| VLDL-C at Day 0 (mg/dl) | 34.10 (11.488) | 39.04 (14.997) | .0752 | .0137 |
| VLDL-C at day 30 (mg/dl) | 31.15 (9.318) | 37.29 (11.541) | .0054 | |
| Mean Difference (mg/dl) | −2.95 | −1.75 | | |
| CI | (−4.455, −1.443) | (−4.116, 0.624) | | |
| P-value[b] | .0003 | .1450 | | |
| VLDL-C at Day 0 (mg/dl) | 34.10 (11.488) | 39.04 (14.997) | .0752 | <.0001 |
| VLDL-C at day 60 (mg/dl) | 28.19 (7.551) | 37.10 (11.587) | <.0001 | |
| Mean Difference | −5.91 | −1.93 | | |
| CI | (−8.203, −3.619) | (−5.299, 1.432) | | |
| P-value[b] | <.0001 | .2536 | | |
| VLDL-C at Day 0 (mg/dl) | 34.10 (11.488) | 39.04 (14.997) | .0752 | .0001 |
| VLDL-C at day 90 (mg/dl) | 26.95 (7.442) | 37.15 (12.835) | <.0001 | |
| Mean Difference | −7.15 | −1.89 | | |

TABLE 6A-continued

Statistical Analysis for Very Low Density Lipoprotein-Cholesterol (VLDL-C) (Per Protocol Population)

| Variable | KaraHeart ™ (N = 47) | Placebo (N = 48) | P-Value[a] | ANCOVA P-Value[c] |
|---|---|---|---|---|
| CI | (−9.529, −4.769) | (−5.671, 1.896) | | |
| P-value[b] | <.0001 | .3207 | | |
| VLDL-C at Day 0 (mg/dl) | 34.10 (11.488) | 39.04 (14.997) | .0752 | <.0001 |
| VLDL-C at day 120 (mg/dl) | 27.20 (8.583) | 38.95 (14.306) | <.0001 | |
| Mean Difference | −6.90 | −0.08 | | |
| CI | (−9.658, −4.138) | (−3.761, 3.594) | | |
| P-value[b] | <.0001 | .9638 | | |

Note:
P Value[a]: Two sample t-test.
P value[b]: Paired t-test
P Value[c]: ANCOVA P Value.

TABLE 6B

Sub-Group Analysis:

| CATEGORY | Variable | KaraHeart ™ Group (N = 47) | Placebo Group (N = 48) | P-Value[a] | ANCOVA P-Value[c] |
|---|---|---|---|---|---|
| VLDL Above 40 mg/dl | N | 12 | 20 | | |
| | BASELINE | 48.97 (6.655) | 53.75 (8.929) | .1193 | .0020 |
| | V6 | 32.67 (7.008) | 48.61 (12.840) | .0001 | |
| | Mean Difference | −16.30 | −5.14 | | |
| | CI | (−20.61, −11.99) | (−11.08, 0.796) | | |
| | P-value[b] | <.0001 | .0858 | | |
| VLDL 32 to 40 mg/dl | N | 18 | 14 | | |
| | BASELINE | 34.56 (2.206) | 34.13 (1.954) | .5727 | .0962 |
| | V6 | 27.64 (8.792) | 33.74 (10.987) | .0911 | |
| | Mean Difference | −6.91 | −0.39 | | |
| | CI | (−11.14, −2.685) | (−7.108, 6.336) | | |
| | P-value[b] | .0031 | .9032 | | |
| VLDL Below 32 mg/dl | N | 17 | 14 | | |
| | BASELINE | 23.12 (7.047) | 22.93 (7.373) | .9425 | .0132 |
| | V6 | 22.87 (7.304) | 30.37 (11.236) | .0329 | |
| | Mean Difference | −0.25 | 7.44 | | |
| | CI | (−3.176, 2.682) | (1.422, 13.464) | | |
| | P-value[b] | .8603 | .0192 | | |

Note:
P Value[a]: Two sample t-test.
P Value[b]: Paired t-test
P Value[c]: ANCOVA P Value.

TABLE 7

Statistical Analysis for Total Cholesterol/HDL-C Ratio (Per Protocol Population)

| Variable | KaraHeart ™ (N = 47) | Placebo (N = 48) | P-Value[a] | ANCOVA P-Value[c] |
|---|---|---|---|---|
| TC/HDL-C at day 0 | 4.92 (1.097) | 5.03 (1.308) | .6650 | .0004 |
| TC/HDL-C at day 30 | 4.67 (0.864) | 5.22 (1.318) | .0202 | |
| Mean Difference | −0.24 | 0.19 | | |
| CI | (−0.386, −0.103) | (−0.044, 0.420) | | |
| P-value[b] | .0011 | .1095 | | |
| TC/HDL-C at day 0 | 4.92 (1.097) | 5.03 (1.308) | .6650 | <.0001 |
| TC/HDL-C at day 60 | 4.51 (0.838) | 5.33 (1.320) | .0006 | |
| Mean Difference | −0.40 | 0.30 | | |
| CI | (−0.567, −0.242) | (0.039, 0.561) | | |
| P-value[b] | <.0001 | .0251 | | |
| TC/HDL-C at day 0 | 4.92 (1.097) | 5.03 (1.308) | .6650 | <.0001 |
| TC/HDL-C at day 90 | 4.38 (0.899) | 5.22 (1.371) | .0007 | |
| Mean Difference | −0.54 | 0.19 | | |
| CI | (−0.732, −0.348) | (−0.108, 0.495) | | |
| P-value[b] | <.0001 | .2028 | | |

TABLE 7-continued

Statistical Analysis for Total Cholesterol/HDL-C Ratio (Per Protocol Population)

| Variable | KaraHeart ™ (N = 47) | Placebo (N = 48) | P-Value[a] | ANCOVA P-Value[c] |
|---|---|---|---|---|
| TC/HDL-C at day 0 | 4.92 (1.097) | 5.03 (1.308) | .6650 | <.0001 |
| TC/HDL-C at day 120 | 4.19 (0.917) | 5.08 (1.350) | .0003 | |
| Mean Difference | −0.73 | 0.06 | | |
| CI | (−0.981, −0.487) | (−0.212, 0.327) | | |
| P-value[b] | <.0001 | .6689 | | |

Note:
P Value[a]: Two sample t-test.
P value[b]: Paired t-test
P Value[c]: ANCOVA P-Value.

TABLE 8A

Statistical Analysis for Triglyceride (Per Protocol Population)

| Variable | KaraHeart ™ (N = 47) | Placebo (N = 48) | P-Value[a] | ANCOVA P-Value[c] |
|---|---|---|---|---|
| Triglycerides at day 0 (mg/dl) | 171.0 (57.249) | 195.2 (74.984) | .0812 | .0114 |
| Triglycerides at day 30 (mg/dl) | 155.7 (46.590) | 186.5 (57.706) | .0054 | |
| Mean Difference (mg/dl) | −15.3 | −8.73 | | |
| CI | (−22.65, −7.900) | (−20.58, 3.120) | | |
| P-value[b] | .0001 | .1450 | | |
| Triglycerides at day 0 (mg/dl) | 171.0 (57.249) | 195.2 (74.984) | .0812 | .0001 |
| Triglycerides at day 60 (mg/dl) | 140.9 (37.756) | 185.5 (57.935) | <.0001 | |
| Mean Difference (mg/dl) | −30.1 | −9.67 | | |
| CI | (−41.41, −18.76) | (−26.49, 7.160) | | |
| P-value[b] | <.0001 | .2536 | | |
| Triglycerides at day 0 (mg/dl) | 171.0 (57.249) | 195.2 (74.984) | .0812 | <.0001 |
| Triglycerides at day 90 (mg/dl) | 134.7 (37.209) | 185.8 (64.177) | <.0001 | |
| Mean Difference (mg/dl) | −36.3 | −9.44 | | |
| CI | (−48.08, −24.47) | (−28.35, 9.479) | | |
| P--value[b] | <.0001 | .3207 | | |
| Triglycerides at day 0 (mg/dl) | 171.0 (57.249) | 195.2 (74.984) | .0812 | <.0001 |
| Triglycerides at day 120 (mg/dl) | 134.3 (40.114) | 194.8 (71.532) | <.0001 | |
| Mean Difference (mg/dl) | −36.7 | −0.42 | | |
| CI | (−49.76, −23.68) | (−18.80, 17.970) | | |
| P-value[b] | <.0001 | .9638 | | |

Note:
P-Value[a]: Two sample t-test.
P-value[b]: Paired t-test
P-Value[c]: ANCOVA P-Value.

TABLE 8B

Sub-group analysis:

| CATEGORY | Variable | KaraHeart ™ Group (N = 47) | Placebo Group (N = 48) | P-Value[a] | ANCOVA P-Value[c] |
|---|---|---|---|---|---|
| TRIGLYCERIDES Above 200 mg/dl | N | 12 | 20 | | .0020 |
| | BASELINE | 244.8 (33.275) | 268.8 (44.646) | .1193 | |
| | V6 | 163.3 (35.041) | 243.1 (64.202) | .0001 | |
| | Mean Difference | −81.50 | −25.70 | | |
| | CI | (−103.0, −59.97) | (−55.38, 3.979) | | |
| | P-value[(b)] | <.0001 | .0858 | | |
| TRIGLYCERIDES 160 TO 200 mg/dl | N | 19 | 14 | | .0361 |
| | BASELINE | 172.3 (10.954) | 170.6 (9.771) | .6636 | |
| | V6 | 133.7 (35.195) | 168.7 (54.937) | .0330 | |
| | Mean Difference | −38.58 | −1.93 | | |
| | CI | (−54.86, −22.29) | (−35.54, 31.682) | | |
| | P-value[(b)] | <.0001 | .9032 | | |

TABLE 8B-continued

Sub-group analysis:

| CATEGORY | Variable | KaraHeart ™ Group (N = 47) | Placebo Group (N = 48) | P-Value[a] | ANCOVA P-Value[c] |
|---|---|---|---|---|---|
| TRIGLYCERIDES Below 160 mg/dl | N | 16 | 14 | | .0159 |
| | BASELINE | 114.2 (35.900) | 114.6 (36.863) | .9729 | |
| | V6 | 113.3 (37.423) | 151.9 (56.182) | .0331 | |
| | Mean Difference | −0.94 | 37.21 | | |
| | CI | (−16.60, 14.724) | (7.109, 67.319) | | |
| | P-value[b] | .9002 | .0192 | | |

Note:
P-Value[a]: Two sample t-test.
P-Value[b]: Paired t-test
P-Value[c]: ANCOVA P-Value.

TABLE 9A

Statistical Summary for Secondary parameters (Per Protocol Population)

| Variable | KaraHeart ™ (N = 47) | Placebo (N = 48) | P-Value[a] | ANCOVA P-Value[c] |
|---|---|---|---|---|
| HbA1C at Day 0 (%) | 5.37 (0.349) | 5.42 (0.410) | .5368 | .2633 |
| HbA1C at Day 120 (%) | 5.54 (0.380) | 5.66 (0.621) | .2423 | |
| Mean Difference | 0.17 | 0.24 | | |
| CI | (0.095, 0.237) | (0.137, 0.347) | | |
| P-Value[b] | <.0001 | <.0001 | | |
| CRP at Day 0 (mg/dl) | 6.54 (1.518) | 6.22 (1.278) | .2571 | .4160 |
| CRP at Day 120 (mg/dl) | 5.96 (1.210) | 6.15 (1.265) | .4604 | |
| Mean Difference | −0.59 | −0.07 | | |
| CI | (−1.160, −0.010) | (−0.543, 0.405) | | |
| P-value[b] | .0463 | .7717 | | |
| ApoA1 at Day 0 (mg/dl) | 136.81 (23.237) | 138.81 (26.285) | .6943 | .0893 |
| ApoA1 at Day 120 (mg/dl) | 142.18 (20.746) | 137.44 (32.879) | .4029 | |
| Mean Difference | 5.37 | −1.37 | | |
| CI | (1.226, 9.512) | (−7.768, 5.022) | | |
| P-value(b) | .0122 | .6678 | | |

Note:
P Value[a]: Two sample t-test.
P value[b]: Paired t-test
P Value[c]: ANCOVA P Value.

TABLE 9B

Sub-group Analysis of ApoA1:

| CATEGORY | Variable | KaraHeart ™ Group (N = 47) | Placebo Group (N = 48) | P-Value[a] | ANCOVA P-Value[c] |
|---|---|---|---|---|---|
| Apolipoprotein A1 above 148 mg/dl | N | 16 | 15 | | .9075 |
| | Day 0 | 161.9 (9.010) | 168.9 (18.765) | .2047 | |
| | Day 120 | 159.0 (17.557) | 165.8 (29.566) | .4330 | |
| | Mean Difference | −2.99 | −3.10 | | |
| | CI | (−11.76, 5.790) | (−16.71, 10.506) | | |
| | P-value[b] | .4795 | .6325 | | |
| Apolipoprotein A1 125 to 148 mg/dl | N | 15 | 18 | | .3694 |
| | Day 0 | 137.8 (5.814) | 135.5 (6.766) | .3088 | |
| | Day 120 | 145.5 (10.117) | 136.5 (24.423) | .1651 | |
| | Mean Difference | 7.70 | 0.94 | | |
| | CI | (2.585, 12.819) | (−9.643, 11.529) | | |
| | P-value[b] | .0061 | .8532 | | |

TABLE 9B-continued

Sub-group Analysis of ApoA1:

| CATEGORY | Variable | KaraHeart ™ Group (N = 47) | Placebo Group (N = 48) | P-Value (a) | ANCOVA P-Value(c) |
| --- | --- | --- | --- | --- | --- |
| Apolipoprotein A1 below 125 mg/dl | N | 16 | 15 | | .0320 |
| | Day 0 | 110.7 (11.903) | 112.6 (13.771) | .6824 | |
| | Day 120 | 122.2 (13.445) | 110.2 (19.226) | .0512 | |
| | Mean Difference | 11.54 | −2.42 | | |
| | CI | (5.249, 17.825) | (−14.34, 9.494) | | |
| | P-value(b) | .0014 | .6695 | | |

Note:
P Value$^a$: Two sample t-test.
P Value$^b$: Paired t-test.
P Value$^c$: ANCOVA P Value.

TABLE 10

Adverse events and dropout subjects.

| Sl. No. | Subject ID | Visit No. | AE Description | Concomitant Medication | Severity | Relationship | Action for IP | Outcome | Group |
| --- | --- | --- | --- | --- | --- | --- | --- | --- | --- |
| 1 | SORA005 | 4 | Constipation | — | Moderate | Not Related | No Action | Completely recovered | Placebo |
| 2 | RMRA020 | 5 | Headache | Diphenhydramine 25 mg + Phenylephrine 5 mg + Caffeine 30 mg | Mild | Not Related | No Action | Completely recovered | KaraHeart ™ |
| 3 | ASSA034 | 4 | Constipation | — | Moderate | Not Related | No Action | Completely recovered | KaraHeart ™ |
| 4 | JBTA043 | 5 | Fever Grade 1 | Acetaminophen 650 mg + Cetirizine 10 mg | Mild | Not Related | No Action | Completely recovered | Placebo |
| 5 | MACA046 | 6 | Diarrhea | Loperamide 2 mg | Mild | Not Related | No Action | Completely recovered | Placebo |
| 6 | BALA086 | 6 | Constipation | | Moderate | Not Related | No Action | Completely recovered | Placebo |
| 7 | BVVA101 | 5 | Itching | Levocetrizine | Mild | Not Related | No Action | Completely recovered | KaraHeart ™ |

While this disclosure includes specific examples, it will be apparent after an understanding of the disclosure of this application has been attained that various changes in form and details may be made in these examples without departing from the spirit and scope of the claims and their equivalents.

The invention claimed is:

1. A composition comprising: *Commiphora mukul* extract, *Camellia sinensis* extract, *Trigonella foenum*-graecum extract, *Allium sativum* extract, *Zingiber officinale* extract, and *Cinnamomum verum* extract, wherein the *Commiphora mukul* extract is about 24% to about 36% by weight of the composition, the *Allium sativum* extract is about 20% to about 30% by weight of the composition, the *Camellia sinensis* extract is about 12% to about 18% by weight of the composition, the *Trigonella foenum*-graecum extract is about 12% to about 18% by weight of the composition, the *Zingiber officinale* extract is about 8% to about 12% by weight of the composition, and the *Cinnamomum verum* extract is about 4% to about 6% by weight of the composition.

2. The composition of claim 1, wherein the *Commiphora mukul* extract is about 30% by weight of the composition, the *Allium sativum* extract is about 25% by weight of the composition, the *Camellia sinensis* extract is about 15% by weight of the composition, the *Trigonella foenum*-graecum extract is about 15% by weight of the composition, the *Zingiber officinale* extract is about 10% by weight of the composition, and the *Cinnamomum verum* extract is about 5% by weight of the composition.

3. The composition of claim 1, wherein the composition further comprises Turmeric extract, Coriander extract, *Capsicum annum* extract, Horse chestnut extract, Rosehip extract, Radish extract, or *Citrus sinensis* extract.

4. The composition of claim 1, wherein an active substance of the *Commiphora mukul* extract comprises Commiphytes, and the composition comprises about 0.6% to about 0.9% Commiphytes by weight.

5. The composition of claim 1, wherein an active substance of the *Camellia sinensis* extract comprises Camitechin, and the composition comprises about 4.8% to about 7.2% Camitechin by weight.

6. The composition of claim 1, wherein an active substance of the *Zingiber officinale* extract comprises Zinzirols, and the composition comprises about 0.4% to 0.6% Zinzirols by weight.

7. The composition of claim 1, wherein
an active substance of the *Commiphora mukul* extract comprises Commiphytes and the composition comprises about 0.75% Commiphytes by weight, an active substance of the *Camellia sinensis* extract comprises Camitechin, and the composition comprises about 6% Camitechin by weight, and an active substance of the *Zingiber officinale* extract comprises Zinzirols, and the composition comprises about 0.5% Zinzirols by weight.

8. The composition of claim 1, wherein the composition further comprises excipients.

9. A method of treating hyperlipidemia in a mammal comprising: administering a composition of claim 1 to a mammal.

10. The method of treating hyperlipidemia in a mammal of claim 9, wherein the hyperlipidemia includes a level of total cholesterol of about 200 mg/dL or more in the mammal's blood.

11. The method of treating hyperlipidemia in a mammal of claim 9, wherein the *Commiphora mukul* extract is about 24% to about 36% by weight of the composition, the *Allium sativum* extract is about 20% to about 30% by weight of the composition, the *Camellia sinensis* extract is about 12% to about 18% by weight of the composition, the *Trigonella foenum*-graecum extract is about 12% to about 18% by weight of the composition, the *Zingiber officinale* extract is about 8%-12% by weight of the composition, and the *Cinnamomum verum* extract is about 4%-6% by weight of the composition.

12. The method of treating hyperlipidemia in a mammal of claim 11, wherein the *Commiphora mukul* extract is about 30% by weight of the composition, the *Allium sativum* extract is about 25% by weight of the composition, the *Camellia sinensis* extract is about 15% by weight of the composition, the *Trigonella foenum*-graecum extract is about 15% by weight of the composition, the *Zingiber officinale* extract is about 10% by weight of the composition, and the *Cinnamomum verum* extract is about 5% by weight of the composition.

13. The method of treating hyperlipidemia in a mammal of claim 9, wherein the composition further comprises Turmeric extract, Coriander extract, *Capsicum* annum extract, Horse chestnut extract, Rosehip extract, Radish extract, or *Citrus sinensis* extract.

14. The method of treating hyperlipidemia in a mammal of claim 9, wherein an active substance of the *Commiphora mukul* extract comprises Commiphytes and the composition comprises about 0.6% to about 0.9% Commiphytes by weight, an active substance of the *Camellia sinensis* extract comprises Camitechin, and the composition comprises about 4.8% to about 7.2% Camitechin by weight, and an active substance of the *Zingiber officinale* extract comprises Zinzirols, and the composition comprises about 0.4% to about 0.6% Zinzirols by weight.

15. The method of treating hyperlipidemia in a mammal of claim 9, wherein the amount of total Cholesterol (TC), low density lipoprotein (LDL), very low density lipoprotein (VLDL), or triglycerides (TGL) in the mammal is reduced.

16. The method of treating hyperlipidemia in a mammal of claim 9, wherein the amount of high-density lipoprotein (HDL) in the mammal is increased.

17. The method of treating hyperlipidemia in a mammal of claim 9, wherein the mammal is a human.

* * * * *